United States Patent
Duebner et al.

(10) Patent No.: US 6,610,871 B1
(45) Date of Patent: Aug. 26, 2003

(54) COPPER-CATALYZED ENANTIOSELECTIVE ALLYLIC SUBSTITUTION REACTIONS

(75) Inventors: Frank Duebner, Friedberg (DE); Paul Knochel, Munich (DE)

(73) Assignee: Avecia Limited, Blackley (GB)

( * ) Notice: Subject to any disclaimer, the term of this patent is extended or adjusted under 35 U.S.C. 154(b) by 0 days.

(21) Appl. No.: 09/763,963

(22) PCT Filed: Aug. 25, 1999

(86) PCT No.: PCT/GB99/02807

§ 371 (c)(1),
(2), (4) Date: May 3, 2001

(87) PCT Pub. No.: WO00/12449

PCT Pub. Date: Mar. 9, 2000

(30) Foreign Application Priority Data

Aug. 28, 1998 (GB) .............................................. 9818701

(51) Int. Cl.[7] .......................... C07F 17/00; C07F 19/00; C07C 5/25

(52) U.S. Cl. ........................ 556/28; 556/144; 556/466; 556/478; 585/665

(58) Field of Search .......................... 556/144, 28, 466, 556/478, 665

(56) References Cited

PUBLICATIONS

Enders, "Enantioselective synthesis of 1–ferrocenylalkylamines via 1,2–addition of organolithium compounds to ferrocenecarboxaldehyde–SAMP–hydrazone", SYNLETT, No. 2, Feb. 1996, pp. 126–128.*

Glorian, "Enantioselective synthesis of (R)–and (S)–ferrocenylalkylamines. Reduction of enantiopure ferrocenylimines obtained from valinol and phenylgycinol", TETRAHEDRON:ASYMMETRY. vol. 8, No. 3, Feb. 6, 1997, pp. 355–358.*

Enders:, "Enantioselective synthesis of 1–ferrocenylalkylamines via 1,2–addition of organolithium compounds to ferrocenecarboxaldehyde–SAMP–hydrazone" SYNLETT, No. 2, Feb. 1996, pp. 126–128, XP002122255.

Glorian:, "Enantioselective synthesis of –and (S)–ferrocenylalkylamines. Reduction of enantiopure ferrocenylimines obtained from valinol and Ihenylgylcinol", TETRAHEDRON: ASYMMETRY., vol. 8, No. 3, Feb. 6, 1997, pp. 355–358, XP002122256, p. 356, last paragragh, p. 357, scheme 3.

Van Klaveren:, "Chiral arenethiolatocopper (I) catalyzed substitution reactions of acyclic allylic substrates with Grignard reagents", TETRAHEDRON LETTERS, vol. 36, No. 17, Apr. 24, 1995, pp. 3059–3062, XP002122257, p. 3060, scheme 2; p. 3061, table I.

Dubner:, "Copper (I)–catalyzed enantioselective substitution of allyl chlorides with diorganozinc compounds", ANGEWANDTE CHEMIE INTERNATIONAL EDITION., vol. 38, No. 2, Feb 1m 1999, pp. 379–381, XP002122258.

Gaudemar: "Preparation D'Esters y–Ethyleniques par allylation du reactif de reformatsky en presence de sels de cuivre", TETRAHEDRON LETTERS, vol. 24, No. 27, pp. 2749–2752, 1983.

Fujii, et al: "Sn2' Selective Alkylation of Allylic Chlorides and Mesylates with RZnX Regagents Generated from Grignards Reagents, Zinc Chloride, Lithium Chloride, and Ce(II)–Salts", TETRAHEDRONS LETTERS, vol. 34, No. 26, pp. 4227–4230, 1993.

* cited by examiner

*Primary Examiner*—Porfirio Nazario-Gonzalez
(74) *Attorney, Agent, or Firm*—Pillsbury Winthrop LLP

(57) ABSTRACT

An allylic compound is reacted with an organozinc compound $Zn(R^6)_2$ to eliminate a group (the leaving group) from the allylic compound and to add a group from the organozinc compound to it in the presence of a copper salt catalyst and a chiral organic ligand for the copper. A novel ferrocenyl compound and a novel copper complex of the ferrocenyl compound and copper are also described.

26 Claims, No Drawings

COPPER-CATALYZED ENANTIOSELECTIVE ALLYLIC SUBSTITUTION REACTIONS

This application is the national phase of international application PCT/GB99/0287 filed Aug. 25, 1999, which designated the U.S.

This invention relates to selective synthesis and catalysts therefor.

According to the invention an allylic compound is reacted with an organozinc compound $Zn(R^6)_2$ to eliminate a group (the leaving group) from the allylic compound and to add a group from the organozinc compound to it in the presence of a copper salt catalyst and a chiral organic ligand for the copper. Preferably the ligand is a primary or secondary amine in which the nitrogen atom is directly linked to the chiral centre. The allylic compound is suitably of formula

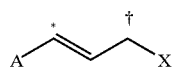

where X is the leaving group for example a chlorine atom and in which A is hydrogen or an alkyl or aryl group, preferably having 1–20 carbon atoms. If substitution occurs at the carbon atom marked * a chiral centre may be formed. This process is known as Sn2' substitution; an alternative substitution at the carbon atom marked † may occur in which case there may be no chiral centre, this process is known as Sn2 substitution.

The reactions are shown as follows:

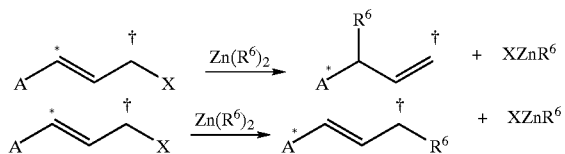

where $R^6$ is a group from the organozinc compound. Surprisingly, in this process the former reaction is generally favoured and is influenced by the leaving group, ligands and solvents as shown below, tetrahydofuran being a particularly favourable solvent. The process is normally chemoselective for Sn2' substitution and/or stereoselective.

In a preferred form of the invention the reaction is as shown below:

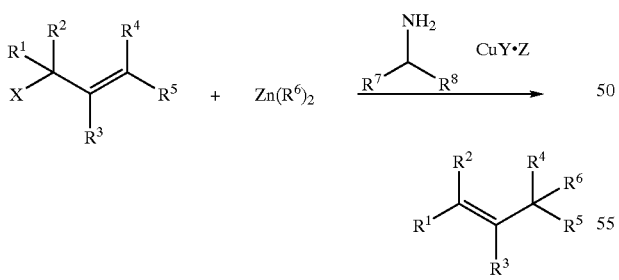

$R^1$–$R^6$ are alkyl, alkenyl, alkynyl, aryl, aralkyl or heterocyclyl groups optionally substituted by for example halogen, alkoxy, aryloxy, acyloxy, nitro, amide, acetamide, carboxylate, cyano, acetal, sulphide, sulphonate, sulfone, sulfoxide, phosphite, phosphonate, phosphine groups, each preferably having at most 20 and preferably less than 10 carbon atoms, or $R^1$ to $R^5$ may be H, $R^7$ is an aryl for example a phenyl or ferrocenyl or substituted aryl or ferrocenyl group of which the substituents may be for example 1-aminobenzyl, 1-amino-2-naphthylmethyl, 1-amino-(4-tert-butylphenyl)methyl, trimethylsilyl, phosphite, phosphine, alkyl, alkoxy, thiophosphonate, amino and/or halogen (eg Cl or Br) atoms and $R^8$ is an alkyl or aryl, preferably a methyl, ethyl, propyl, tert-butyl, phenyl or naphthyl for example 2-naphthyl group which may be substituted for example by nitro, alkoxy, alkyl and/or haloalkyl group. X is halogen, $OR^9$, $OCOR^9$, $OCO_2R^9$, $OSO_2R^9$, $OCS_2R^9$ $CH(OR^{10})_2$, $OPO(OR^9)_2$, $SOR^9$, or $SO_2R^9$ where $R^5$ and $R^{10}$ are optionally substituted $C_1$–$C_{10}$ alkyl or aryl, of which the substituents may be halogen, nitro, methoxy, trifluoromethoxy, methyl, ethyl, tert butyl or sulphonate groups e.g. methyl, ethyl, trifluoromethyl, phenyl, tosyl, p-bromophenyl, p-nitrophenyl, p-methoxyphenyl, or R7 and R8 may together form a 5 or 6 membered carbocyclic or heterocyclic ring providing that a carbon atom to which the nitrogen is attached is chiral. for example R7 and R8 together may be 1-indane, bornylamine or 2-cyclohexylamine. Y is halogen, carboxylate for example, acetate, acetoacetate, cyanide, or thiocyanate and Z is an ether or thioether for example dimethylsulfide, tetrahydrofuran or diethylether. Preferably $R^1$–$R^2$ and $R^3$ and one of $R^4$ or $R^5$ are H and the other one of $R^4$ or $R^5$ is aryl, for example phenyl, 4-chlorophenyl or 4-trifluoromethyl phenyl or is a trialkyl (e.g. tri-isopropyl) silyl oxymethyl groups $R^6$ is alkyl, tri-alkyl (e.g. trimethyl) silyl methyl, phenyl or 2,2-dimethylbut-3-enyl. $R^7$ is ferrocenyl, $R^8$ is naphthyl, X is chloride, Y is chloride or bromide and Z is dimethylsulfide. $R^5$ is preferably phenyl and $R^6$ is preferably neopentyl. The substituents of $R^7$ preferably have at most 10 carbon atoms in total and those of $R^8$ preferably at most 8 carbon atoms in total. Alkanes, cyclo alkanes and/or aromatic solvents for example toluene may be present.

Preferred solvents are ethers for example diethylether, 1,4-dioxane, tertbutylmethylether and especially tetrahydrofuran. Preferred temperatures are –120° C. to 25° C. more preferably –100° C. to 20° C. and especially –90° C. to –50° C.

Preferred concentrations of catalyst are 0.1 atom % to 20 atom %, especially 0.5 atom % to 5 atom % expressed as copper atoms based on moles of the allylic compound.

The ratio of copper atoms to the amine ligand molecules is suitably 1:10 to 2:1.

Compounds for formula

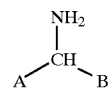

in which A is a ferrocenyl or substituted ferrocenyl group and B is a group $R^8$ other than a methyl or phenyl group are believed to be novel. The groups A and B should be different in order to obtain stereospecificity. B is preferably a 2-naphthyl group.

EXAMPLE 1

Preparation of (R)-(1-amino-2-naphthylmethyl) Ferrocene

Step 1

Ferrocene (4.5 g, 24 mmol) and aluminium trichloride (3.5 g, 26 mmol) were combined in dry dichloromethane (100 ml) at 0° C. under argon. To the greenish suspension was added a solution of 2-naphthoyl chloride (5.0 g, 26 mmol) in dichloromethane (20 ml) at 0° C. over a period of 20 min to obtain a dark purple solution. The reaction was stirred for 2 h at room temperature and then quenched by careful addition of saturated aqueous ammonium chloride solution (100 ml). The organic layer was separated, washed with sat. aqueous sodium bicarbonate solution (2×30 ml), dried (MgSO$_4$) and concentrated under reduced pressure. The crude residue was purified by column chromatography on silica gel using 1:1 pentane: diethyl ether by volume as eluent to give the ketone (5.6 g, 69%) as a red solid.

Step 2

The ferrocenyl ketone (4.5 g, 13.2 mmol) and borane dimethyl sulfide complex (1.4 ml, 14 mmol) were added simultaneously over a period of 30 minutes to a solution of the CBS catalyst (0.70 g, 2.5 mmol) in THF (80 ml) at 0° C. under argon. CBS catalyst is

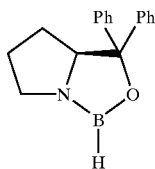

The catalyst is prepared from 1,1-diphenyl pyrrolidine methanol and borane (see Synlett 1993, 929).

After stirring for an additional 30 min the mixture was quenched with aq. ammonium chloride solution (70 ml). The organic layer was separated, dried (MgSO$_4$) and concentrated under reduced pressure. The crude product was purified by column chromatography on silica gel using 1:1 pentane:ether as eluent affording the desired alchohol (4.0 g, 89%) as an orange solid.

Step 3

The ferrocenyl alcohol (4.0 g, 11.6 mmol) was dissolved in dry pyridine (30 ml) and acetic anhydride (20 ml) at room temperature. After stirring for 18 h at room temperature all volatiles were removed under high vacuum at 50° C. furnishing the pure acetylated alcohol (4.5 g, 100%) as a red glue, that smoothly crystallised on standing to a red solid.

The acetylated alcohol (3.0 g, 8 mmol) was dissolved in acetonitrile (200 ml) and 37% aqueous ammonia solution (40 ml). After stirring for 24 h at room temperature the mixture was poured into 10% aqueous hydrochloric acid (200 ml). The resulting precipitate was removed by filtration and washed with ether (4×20 ml). The residue was dissolved in 20% aqueous sodium hydroxide solution (200 ml) and the desired product re-extracted with ether (5×50 ml). After drying (MgSO$_4$), the solvent was removed under reduced pressure and the pure (R)-(1-amino-2-naphthylmethyl) ferrocene (1.8 g, 66%) was obtained as an orange solid.

The corresponding compounds in which the naphthyl group is replaced by phenyl, o-tolyl, 1-naphthyl, 2-naphthyl, methyl, cyclohexyl, o-biphenyl, p-biphenyl, phenanthrenyl, o-bromophenyl and p-butylphenyl were prepared similarly. Compounds in which the ferrocenyl is symmetrically 1,1'-disubstituted with 1-aminobenzyl, 1-amino-2-naphthylmethyl, 1-amino-(4-tert-butylphenyl)methyl, or 2-substituted with trimethylsilyl were prepared using the method given in example 1 except that two mole equivalents of aluminium chloride and acylchloride were used in step 1, two mole equivalents borane dimethylsulfide and 30 mol % CBS catalyst were used in step 2, and two mole equivalents acetic anhydride, pyridine and ammonia were used in step 3. The enantiomeric excess was in each case greater than 99%.

The reaction is illustrated below. The reaction was also carried out with the compounds indicated below, the % figures indicating the stated yields of pure material based on starting material,

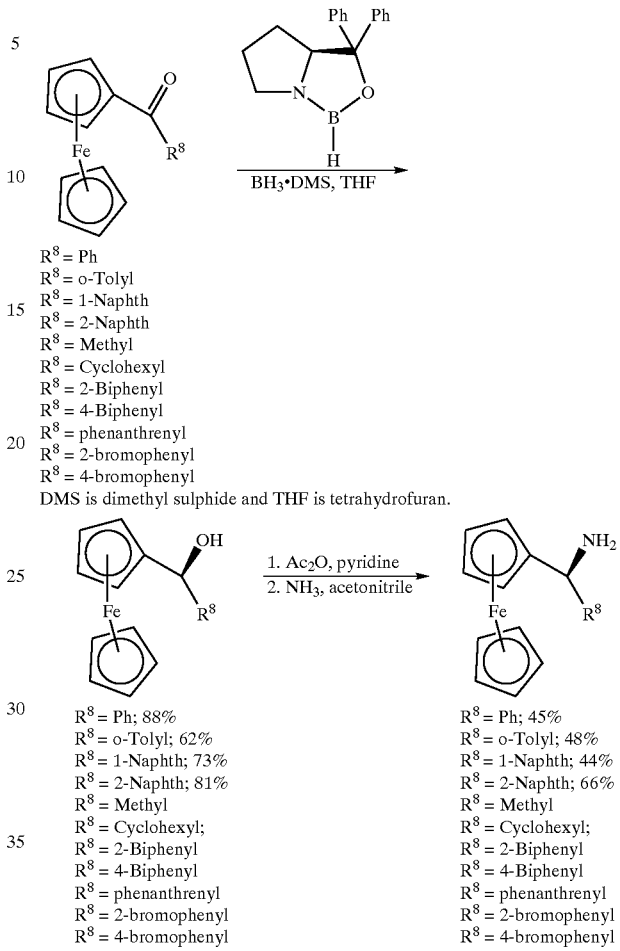

$R^8$ = Ph
$R^8$ = o-Tolyl
$R^8$ = 1-Naphth
$R^8$ = 2-Naphth
$R^8$ = Methyl
$R^8$ = Cyclohexyl
$R^8$ = 2-Biphenyl
$R^8$ = 4-Biphenyl
$R^8$ = phenanthrenyl
$R^8$ = 2-bromophenyl
$R^8$ = 4-bromophenyl
DMS is dimethyl sulphide and THF is tetrahydrofuran.

$R^8$ = Ph; 88%
$R^8$ = o-Tolyl; 62%
$R^8$ = 1-Naphth; 73%
$R^8$ = 2-Naphth; 81%
$R^8$ = Methyl
$R^8$ = Cyclohexyl;
$R^8$ = 2-Biphenyl
$R^8$ = 4-Biphenyl
$R^8$ = phenanthrenyl
$R^8$ = 2-bromophenyl
$R^8$ = 4-bromophenyl $R^8$ = Ph; 45%
$R^8$ = o-Tolyl; 48%
$R^8$ = 1-Naphth; 44%
$R^8$ = 2-Naphth; 66%
$R^8$ = Methyl
$R^8$ = Cyclohexyl;
$R^8$ = 2-Biphenyl
$R^8$ = 4-Biphenyl
$R^8$ = phenanthrenyl
$R^8$ = 2-bromophenyl
$R^8$ = 4-bromophenyl

EXAMPLE 2

Enantioselective allylation. Preparation of (+)-(S)-5,5-dimethyl-3(4-trifluoromethylphenyl)-1-hexene This reaction is shown below

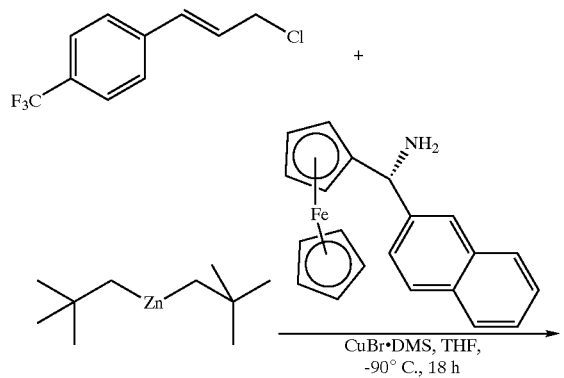

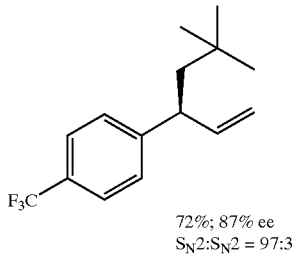

72%; 87% ee
$S_N2:S_N2' = 97:3$

The chiral organic ligand $R^7$=ferrocenyl, $R^8$=2-naphthyl (70 mg, 0.2 mmol) and $CuBr.Me_2S$ (3 mg, 0.02 mmol) were dissolved in THF (5 ml) yielding a clear solution. After cooling to −90° C., neo-$Pent_2Zn$ (0.3 ml, 2.4 mmol) and 4-trifluoromethylcinnamyl chloride were added successively. The reaction mixture was stirred for 18 h at −90° C. and was worked up. The crude residue obtained after evaporation of the solvents was purified by flash-chromatography (ether:pentane 1:50) leading to the desired product (370 mg, 72% yield: $S_N2'/S_N2$ ratio:97:3). The enantiomeric excess of the chiral product was determined by gas chromatography to be 87% using a Chiraldex capillary column.

Use of different substituents $R^7$ and $R^8$ in asymmetric allylation reaction

The following Table 1 shows the use of different chiral organic ligands (lig*) $R^7$ and $R^8$ as indicated in table 1, in the reaction of cinnamyl chloride with di-neopentyl zinc at −50° C. The chiral organic ligands were prepared according to the methods in example 1 and are of the (R) configuration. The experimental conditions are analogous to those in Example 2 above.

TABLE 1

| Entry | $R^7$ | $R^8$ | Yield % | $S_N2':S_N2$ | ee |
|---|---|---|---|---|---|
| 1 | Ferrocenyl | Phenyl | 73 | 95:5 | 32% |
| 2 | Ferrocenyl | o-Tolyl | 79 | 96:4 | 16% |
| 3 | Ferrocenyl | 1-Naphthyl | 72 | 93:7 | 33% |
| 4 | Ferrocenyl | 2-Naphthyl | 77 | 95:5 | 42% |
| 5 | Ferrocenyl | Methyl | 74 | 88:12 | 7% |
| 6 | Ferrocenyl | Cyclohexyl | 74 | 92:8 | 15%[1] |
| 7 | Ferrocenyl | o-Biphenyl | n.d. | 92:8 | 4% |
| 8 | Ferrocenyl | p-Biphenyl | 84 | 97:3 | 38% |
| 9 | Ferrocenyl | Phenanthrenyl | 69 | 98:2 | 61% |
| 10 | Ferrocenyl | 2-Naphthyl | 75 | 97:3 | 67% |
| 11 | Ferrocenyl | o-Bromophenyl | 67 | 96:4 | 38% |
| 12 | Ferrocenyl | p-'Butylphenyl | 69 | 96:4 | 56% |
| 13 | (structure: Ph-CH(NH2)-ferrocenyl-$R^8$) | Ph-CH(NH2)- | 68 | 99:1 | 51% |
| 14 | (structure: 2-naphthyl-CH(NH2)-ferrocenyl-$R^8$) | 2naphthyl-CH(NH2)- | 68 | 97:3 | 52% |
| 15 | (structure: 4-tBu-phenyl-CH(NH2)-ferrocenyl-$R^8$) | tertbutylphenyl-CH(NH2)- | 69 | 96:4 | 45% |

TABLE 1-continued

| Entry | R⁷ | R⁸ | Yield % | $S_N2':S_N2$ | ee |
|---|---|---|---|---|---|
| 16 | 2-methylferrocenyl-Si[Me]₃ | 1-(2-naphthyl)ethylamine | 66 | 98:2 | 11% |
| 17 | phenyl | methyl | >95 | 94:6 | 44% |
| 18 | 2-naphthyl | methyl | >95 | 95:5 | 42% |
| 19 | 1-naphthyl | methyl | >95 | 95:5 | 52% |
| 20 | R⁷ + R⁸ = (R)-2-bornyl | | 80% | 86:14 | 18% |
| 21 | R⁷ + R⁸ = (R)1-indanyl | | >95% | 93:7 | 16% |
| 22 | R⁷ + R⁸ = (S)-trans-2-cyclohexylamine | | 70% | >99:1 | 0% |
| 23 | (S)-2-aminobenzyl | phenyl | 70% | >99:1 | 0% |

Entry 1–8: Ratio CuBr Me₂S/Lig*/Substrate = 1/1/20. Entry 9-23:1/10/100
[1]Opposite stereoisomer in excess Use of different substrates for the substitution The following Tables 2 and 3 show the use of different allyl reagents R¹ and R² and (except in entry 13 of Table 3) R³ = H, R⁴ and R⁵ as indicated in the tables, in the reaction with di-neopentyl zinc using the chiral ligand R⁷ = ferrocenyl, R⁸ = 2-naphthyl of the (R) configuration. The experimental conditions are analogous to those in Example 2 above.

Reactions run at −50° C.

TABLE 2

Reactions run at −50° C.

| Entry | R⁴ | R⁵ | Yield (%) | $S_N2':S_N2$ | ee |
|---|---|---|---|---|---|
| 1 | H | phenyl | 75 | 97:3 | 67% |
| 2 | phenyl | H | 50 | 96:4 | 22% |
| 3 | H | 2-trifluoromethyl phenyl) | 55 | 80:20 | —[1] |
| 4 | H | 4-trifluoromethyl phenyl) | 70 | 98:2 | 74% |
| 5 | H | 1-naphthyl | 74 | 97:3 | 58% |
| 6 | H | cyclohexyl | 70 | (78:22) | 59% |
| 7 | H | phenylmethyl | 50 | 18:82 | 4% |
| 8 | CH₂OMe | H | 67 | >99:1 | 2% |
| 9 | CH₂OAc | H | 74 | >99:1 | 14% |
| 10 | CH₂OSitBuMe₂ | H | 30 | >99:1 | 29% |
| 11 | CH₂OSi(iPr)₃ | H | 53 | >99:1 | 47% |
| 12 | H | CH₂OSi(ipr)₃ | 55 | >99:1 | 38% |
| 13 | CH₂OSiPh₂tBu | H | 70 | >99:1 | 12% |

[1]Separation of enantiomers was not possible.

Reactions run at −90° C.

TABLE 3

Reactions run at −90° C.

| Entry | R⁴ | R⁵ | R³ | Yield (%) | $S_N2':S_N2$ | ee |
|---|---|---|---|---|---|---|
| 1 | H | phenyl | H | 68 | 95:5 | 82% |
| 2 | H | 4-trifluoromethyl phenyl | H | 72 | 97:3 | 87% |
| 3 | H | 1-naphthyl | H | 65 | 94:6 | 71% |
| 4 | H | 2-naphthyl | H | 60 | 91:9 | 70% |
| 5 | H | cyclohexyl | H | 67 | 98:2 | 76% |
| 6 | H | 3-thienyl | H | 70 | 94:6 | 63% |
| 7 | CH₂OSi(iPr)₃ | H | H | 45 | >99:1 | 64% |
| 8 | H | 4-isopropylphenyl | H | 70 | 90:10 | 76% |
| 9 | H | 4-chlorophenyl | H | 71 | 96:4 | 79% |
| 10 | H | 3-chlorophenyl | H | 72 | 97:3 | 70% |
| 11 | H | 3,4-dichlorophenyl | H | 68 | 96:4 | 22% |
| 12 | H | 1-cyclopentenyl | H | 63 | 64:36 | 60% |
| 13 | phenyl | H | —CO₂Et | 71 | 87:13 | 12% |

Use of different diorganozincs at −50° C.

The following Table 4 shows the use of different organozinc reagents $Zn(R^6)_2$, in the reaction with trans-cinnamyl chloride using the chiral ligand $R^7$=ferrocenyl, $R^8$=2-naphthyl of the (R) configuration. The experimental conditions are analogous to those in Example 2 above.

TABLE 4

| Entry | $R^6$ | Yield (%) | $S_N2':S_N2$ | ee |
|---|---|---|---|---|
| 1 | Methyl | 90 | 98:2 | 10% |
| 2 | Ethyl | 88 | 98:2 | 10% |
| 3 | isoPropyl | 87 | 98:2 | 29% |
| 4 | isoButyl | 69 | 98:2 | 45% |
| 5 | Pentyl | 88 | 98:2 | 26% |
| 6 | neoPentyl | 75 | 97:3 | 67% |
| 7 | 1R-(+)-Pinane | 65 | 97:3 | 41% |
| 8 | 1S-(−)-Pinane | 60 | 98:2 | 37% |
| 9 | $PhMe_2SiCH_2$ | 50 | 90:10 | 42% |
| 10 | $Me_3SiCH_2$ | 52 | 94:6 | 67% |
| 11 | $Me_2PhCCH_2$ | —[1] | 68:32 | 25% |
| 12 | $Me_2PhSi(CH_2)_2$ | 78 | 98:2 | 15% |
| 13 | $H_2C=CH_2C(CH_3)_2CH_2$ | 65 | 95:5 | 79%[2] |

[1]Reaction worked up before completion. [2]Reaction done at −85° C.

What is claimed is:

1. A process in which an allylic compound is reacted with an organozinc compound to eliminate a group (the leaving group) from the allylic compound and to add a group from the organozinc compound to it in the presence of a copper salt catalyst and a chiral organic ligand for the copper.

2. A process as claimed in claim 1 in which the allylic compound is of formula

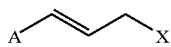

where X is the leaving group and in which A is hydrogen or an alkyl or aryl group, having 1–20 carbon atoms.

3. A process as claimed in claim 1 or 2 in which $S_N2'$ substitution giving a chiral centre occurs.

4. A process as claimed in either claim 1 or claim 2 in which the reaction is stereospecific.

5. A process as claimed in claim 1 in which the reaction is as follows

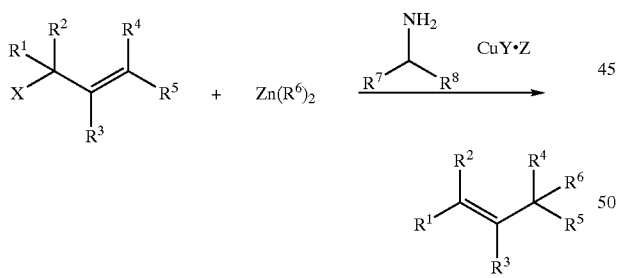

wherein $R^1$–$R^6$ are alkyl, alkenyl, alkynyl, aryl, aralkyl or heterocyclyl groups optionally substituted by halogen, alkoxy, aryloxy, acyloxy, nitro, amide, acetamide, carboxylate, cyano, acetal, sulphide, sulphonate, sulfone, sulfoxide, phosphite, phosphonate, phosphine groups, each having at most 20 carbon atoms or $R^1$ to $R^5$ may be H, $R^7$ is an aryl and $R^8$ is an alkyl or aryl, which may be substituted, X is halogen, $OR^9$, $OCOR^9$, $OCO_2R^9$, $OSO_2R^9$, $OCS_2R^9$ $CH(OR^{10})_2$, OPO $(OR^9)_2$, $SOR^9$, or $SO_2R^9$ in which $R^9$ and $R^{10}$ are optionally substituted $C_1$–$C_{10}$ alkyl or aryl, Y is halogen, carboxylate, cyanide, or thiocyanate and Z is an ether or thioether.

6. A process as claimed in claim 5 in which $R^8$ is aryl optionally substituted by a halogen or haloalkyl group.

7. A process as claimed in claim 5 in which $R^1$, $R^2$, $R^3$ and one of $R^4$ and $R^5$ are hydrogen the other of $R^4$ and $R^5$ is an aryl or trialkylsilyloxymethyl group, $R^6$ is an alkyl group and $R^7$ is a ferrocenyl group, $R^8$ is an aryl group.

8. A process as claimed in claim 6 in which $R^8$ is a naphthyl or substituted naphthyl group.

9. A process as claimed in claim 5 in which X is chlorine and Y is chloride or bromide.

10. A process as claimed in claim 5 in which $R^1$, $R^2$, $R^3$ and one of $R^4$ and $R^5$ are hydrogen, and in which the other of $R^4$ and $R^5$ is a phenyl,4-chlorophenyl, 4-trifluoromethyl phenyl, or trialkyl silyl oxy methyl group.

11. A process as claimed in claim 5 in which one of the groups $R^7$ or $R^8$ is a ferrocenyl or substituted ferrocenyl group and the other is a naphthyl or substituted naphthyl group.

12. A process as claimed in claim 5 in which $R^5$ is a phenyl group and $R^6$ is a neopentyl group.

13. A process as claimed in claim 1 or claim 2 in which an alkane, cyclo alkane and/or aromatic solvent is present.

14. A process as claimed in claim 1 or claim 2 in which an ether is present as a solvent.

15. A process as claimed in claim 14 in which the ether is diethylether, 1,4-dioxane, tertbutylmethylether, or tetrahydrofuran.

16. A process as claimed in claim 1 or claim 2 which is carried out at a temperature of −90° C. to −50° C.

17. A process as claimed in claim 1 or claim 2 in which the concentration of the catalyst is in the range 0.5 to 5 atom %, expressed as copper atoms based on moles of the allylic compound.

18. A process as claimed in claim 1 or claim 2 in which the ratio of copper atoms to the amine ligand molecules is 1:10 to 2:1.

19. A compound of formula

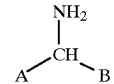

in which A is a ferrocenyl or substituted ferrocenyl group and B is an aryl group other than a phenyl group.

20. A compound as claimed in claim 19 in which B is a 2-naphthyl group.

21. A complex which comprises a compound of formula

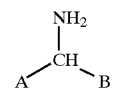

in which A is a ferrocenyl or substituted ferrocenyl group and B is an alkyl group or aryl group other than a methyl group or phenyl group, and copper.

22. A complex according to claim 21, wherein B is an aryl group other than phenyl.

23. A complex according to claim 21, wherein B is a 2-naphthyl group.

24. A process as claimed in claim 6 in which $R^8$ is phenyl optionally substituted by a halogen or haloalkyl group.

25. A process as claimed in claim 5 where each of $R^1$ to $R^6$ have less than 10 carbon atoms.

26. A process as claimed in claim 5 wherein $R^7$ is phenyl or ferrocenyl or substituted aryl or ferrocenyl groups.

* * * * *